United States Patent [19]

Tomislav et al.

[11] Patent Number: 5,128,487

[45] Date of Patent: Jul. 7, 1992

[54] PROCESS FOR THE PRODUCTION OF SODIUM OR POTASSIUM L-ASCORBATE

[75] Inventors: Keglevic Tomislav, Gumpoldskirchen, Austria; Klein Christoph, Zurich, Switzerland

[73] Assignee: Enco Engineering Chur AG, Chur, Switzerland

[21] Appl. No.: 542,447

[22] Filed: Jun. 22, 1990

[30] Foreign Application Priority Data

Jun. 26, 1989 [CH] Switzerland ............... 2377/89

[51] Int. Cl.$^5$ ........................... C07D 307/62
[52] U.S. Cl. ................................ 549/315
[58] Field of Search ........................... 549/315

[56] References Cited

U.S. PATENT DOCUMENTS

| | | | |
|---|---|---|---|
| 2,179,978 | 11/1939 | Elger | 548/315 |
| 2,462,251 | 2/1949 | Bassford et al. | 549/315 |
| 4,180,511 | 12/1979 | Crawford | 549/315 |

FOREIGN PATENT DOCUMENTS 1468267  6/1963  Fed. Rep. of Germany .

*Primary Examiner*—Jane T. Fan
*Assistant Examiner*—Amelia A. Owens
*Attorney, Agent, or Firm*—Tarolli, Sundheim & Covell

[57] ABSTRACT

In the process described for the production of sodium or potassium L-ascorbate, 2-keto-L-gulonic acid monhydrate is esterified with methanol. The esterification is only partial, that is, is not carried out until the esterification equilibrium is reached. In an intermediate step, by addition of sodium or potassium bicarbonate in an amount precisely enough for neutralizing the esterified solution, unesterified 2-keto-L-gulonic acid and impurities present are precipitated and separated out. Then by adding more bicarbonate, the lactonizing of the 2-keto-L-gulonic acid methyl ester formed is made possible. In order to reach a high yield, the unesterified 2-keto-L-gulonic acid from the bicarbonate precipitation may be re-esterified by the same process, preferably parallel, and also converted into ascorbate. This process makes possible the production of very pure sodium or potassium ascorbate, suitable for pharmaceutical purposes in a profitable way.

12 Claims, 1 Drawing Sheet

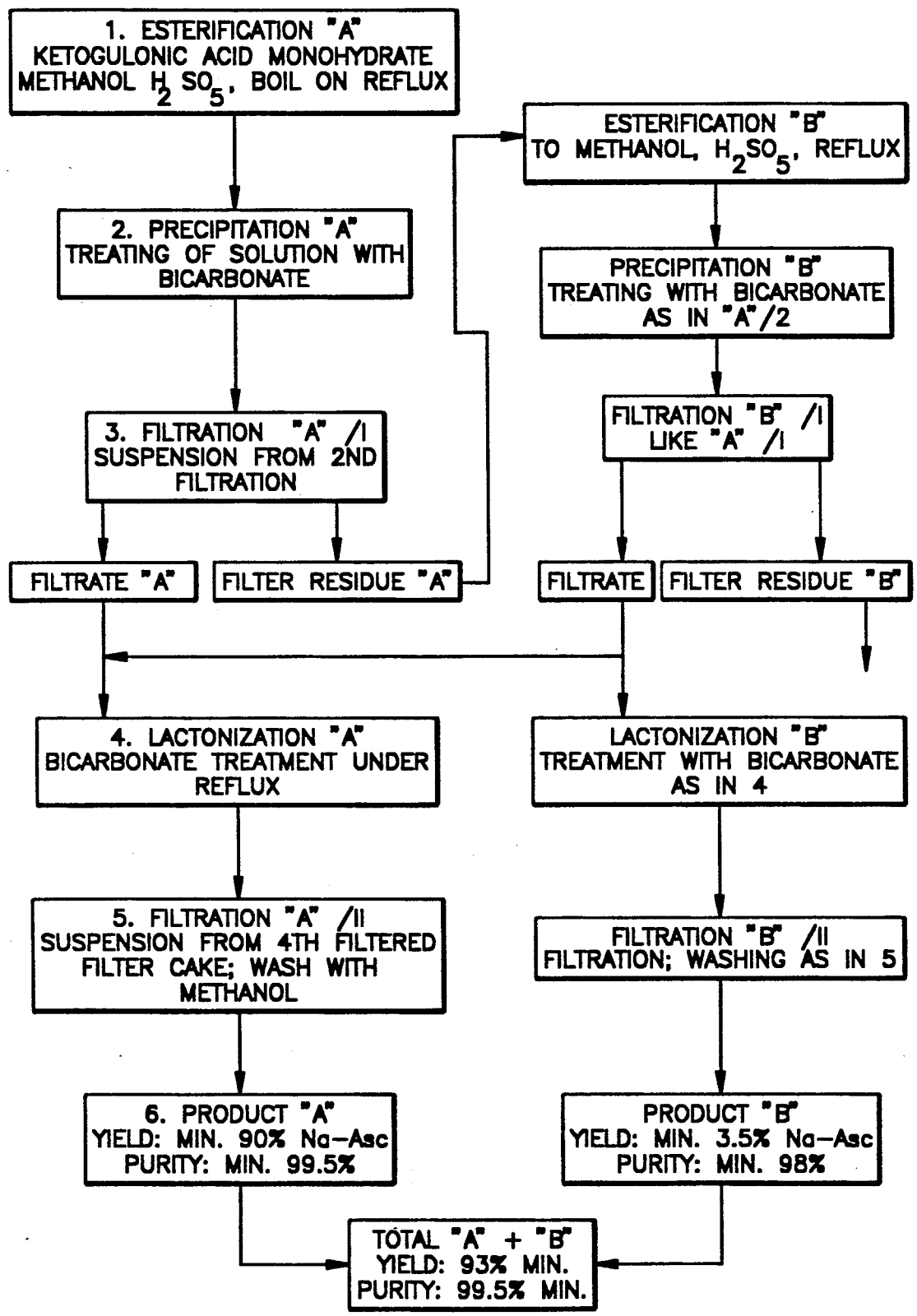

PROCESS FOR THE PRODUCTION OF SODIUM OR POTASSIUM L-ASCORBATE

TECHNICAL FIELD

This invention relates to a process for the production of sodium or potassium L-ascorbate, with the use of 2-keto-L-gulonic acid, in which 2-keto-L-gulonic acid methyl ester is formed and lactonated by the addition of bicarbonate.

STATE-OF-THE-ART

Sodium L-ascorbate is used in industrial practice, for example, as an intermediate product, in the production of L-ascorbic acid, generally using a more or less modified so-called Reichstein Process (T. Reichstein, A. Grussner, Helv. Chim. Acta 17, p. 311, 1934). In this process, di-iso-propylidene-2-keto-L-gulonic acid monohydrate is produced in an earlier reaction step, as an intermediate product. This methyl ester is converted by lactonizing, by addition of sodium bicarbonate, into sodium L-ascorbate from which, finally, L-ascorbic acid is obtained.

In principle, the esterification equilibrium limits the yield. In the Reichstein process, usually a long boiling time is chosen to obtain a high degree of esterification and thus a satisfactory yield. However, this has an adverse effect on purity. Both the 2-keto-L-gulonic acid and the methyl ester are no longer heat-stable. They can decompose readily at the necessary reaction temperature. The products of decomposition as well as the unreacted 2-keto-L-gulonic acid are impurities in the end product, the removal of which entails considerable expense. For the production of sodium L-ascorbate as an end product in sufficient purity for pharmaceutical purposes, therefore, the Reichstein process is not suitable or at least not profitable.

In the fermentative production of 2-keto-L-gulonic acid monohydrate, there occurs also the problem of removal of the soluble proteins from the product of fermentation. These proteins also become impurities in the final product. They can only be separated, whether by crystallization or by ion exchanges, at considerable unprofitable expense and with loss of product.

For the production of sufficiently pure sodium or potassium L-ascorbate, in view of the problems explained above, usually L-ascorbic acid of sufficient purity is used as starting material.

DESCRIPTION OF THE INVENTION

The problem of the present invention is to provide a process for the production of sodium or potassium L-ascorbate, with the use of 2-keto-L-gulonic acid, which permits obtaining the desired end product with sufficient purity in an economical way.

This and other problems are solved, according to the present invention, by a process as distinguished in claim 1.

In the process of the invention, in particular, the esterification of the 2-keto-L-gulonic acid, with methanol, is only partly carried out, that is, not until the esterification equilibrium is reached. The process of the invention requires, therefore, only very short reaction times in the esterification by utilization of the zone of high reaction speed and by excluding the zones of low reaction speed. With this is associated, advantageously, a much lower occurrence of decomposition products.

Moreover, in an intermediate step, by addition of sodium bicarbonate or potassium bicarbonate according to the end product desired is an amount substantially just sufficient for neutralization of the esterified solution, unesterified 2-keto-L-gulonic acid and impurities present are precipitated from the solution and separated. Only then by addition of more bicarbonate is the lactonization of the 2-keto-L-gulonic acid methyl ester, which only takes place in the alkaline zone, made possible.

The process of the invention is distinguished by a high purity of the esterified solution. Unreacted 2-keto-L-gulonic acid and impurities, such as the decomposition products mentioned, and also the soluble proteins mentioned before which result from the fermentative production of the 2-keto-L-gulonic acid monohydrate, are precipitated in the intermediate step and separated.

The process of the invention makes possible the direct production of pure sodium or potassium L-ascorbate in the course of the L-ascorbic acid synthesis.

Finally, the process of the invention makes possible, through the short reaction times, a profitable continuous production of 2-keto-L-gulonic acid methyl ester.

Advantageous and preferred further developments of the process of the invention are distinguished in the dependent claims.

For obtaining 2-keto-L-gulonic acid methyl ester, a mixture of 2-keto gulonic acid monohydrate and sodium-2-keto gulonate may be used in which the proportion of sodium salt may be up to 30%. A mixture of 50% monohydrate and 50% salt is more stable than the pure monohydrate. In case of a high proportion of salt, the salt must first be transformed into the acid, which is done by adding a sufficient amount of sulfuric acid. The resultant sulfate is preferably separated out before the addition of bicarbonate. This separation may take place, with advantage, even before the addition of concentrated sulfuric acid catalysing the esterification. So long as the proportion of sodium salt put into the mixture is not too high and may amount to only a few percent, the separate removal of the sulfate may also be omitted. It is then removed with the precipitate caused by the addition of bicarbonate.

It suffices to drive the esterification only up to a degree of 87–91%.

Preferably, for the esterification, a temperature in the range from 62° to 75° C. is set.

Esterification is carried out in the presence of concentrated sulfuric acid in catalytic amounts for acceleration of the reaction, preferably within 15 to 90 minutes, according to the degree of impurity of the starting product.

The amount of bicarbonate necessary for causing the precipitation must be sufficient not only for the neutralization of the 2-keto-L-gulonic acid, but additionally, for the neutralization of the sulfuric acid put in.

Preferably, the bicarbonate is added in slight excess (above the exact amount needed for neutralization per se) of 1% to 2%, to the esterification process. During and after the addition of bicarbonate, preferably at a constant temperature of about 60° C., it is stirred for ½ to 2 hours.

The separation of precipitate takes place, preferably through filtering, but in principle any solid-fluid separation method can be used.

The sodium or potassium bicarbonate necessary for lactonizing may be added directly to the esterified solution obtained after separating out the precipitate.

For the production of highly pure ascorbate, however, the following route may also be taken. The esterified solution obtained after separating the precipitate is cooled (to about 0° C.), and then, in the pure form (partly) precipitating ester as preferably separated again by filtration. The esterification obtained in the pure form is dissolved in methanol, and the process is carried on with this esterified solution.

But the process may also be carried on with the mother fluid from which the methyl ester has been precipitated (partly) by cooling, since this latter still contains enough methyl ester. The ascorbate obtained in this way is less pure, however, but it can still be used for certain purposes.

For the lactonizing of 2-keto-L-gulonic acid methyl ester, the solution containing it, after the addition of more sodium or potassium bicarbonate, is preferably boiled for only 30 to 180 minutes at 60° to 67° C.

The sodium or potassium L-ascorbate obtained in suspension is preferably separated again by filtering.

The separated ascorbate may also be washed with methanol again to advantage.

The yield obtainable can be advantageously increased by the fact that precipitate separated in the above-mentioned intermediate step is used again as starting material instead of fresh 2-keto-L-gulonic acid monohydrate. The separated precipitate which, according to the degree of esterification reached, still contains 3% to 10% of the unesterified starting product is dissolved in methanol instead of fresh 2-keto-L-gulonic acid monohydrate, preferably in a separate solution, and in the same way as described above, is subjected to esterification, precipitation and separation of the deposit. It now contains only insignificant amounts of starting product but relatively higher concentration in undesirable impurities.

The remaining fluid, which contains 2-keto-L-gulonic acid methyl ester, is then either added to the original lot, leaving the same kind of fluid after separation of the deposit, and thus introduced again into the original process, or else separately processed, but in the same manner, to ascorbate.

The precipitate separated from the original esterified solution (the primary lot of solution) being added, not separately, but together with fresh keto-2-L-gulonic acid monohydrate, is possible but not so advantageous. The content in impurities in the primary lot of solution is increased in this way. Also, the filterability of the primary lot of solution is poorer and thus more time-consuming and expensive.

A few examples are given below for the process according to the invention in which reference is made also to the attached scheme. The examples all concern the production of sodium L-ascorbate, but may be used in the same way for potassium L-ascorbate, if instead of the amounts in grams or cubic centimeters, the corresponding mols are given.

EXAMPLE 1

One hundred grams 2-keto-gulonic acid monohydrate (98.3%) is dissolved in 300 cc methanol (maximum 0.2% $H_2O$) with 4.5 cc $H_2SO_4$ (98%), and esterified for 30 minutes at 67° to 68° C.) (Esterification A). Then the solution is treated at 60° C. with 12.5 g sodium bicarbonate (99%), and stirred two hours at constant temperature (Precipitation A). The precipitate formed is filtered out (Filtration A/I). The Filtrate (Filtrate A) is then lactonized for two hours with more bicarbonate (Lactonization A). The resultant ascorbate (Product A) is finally isolated by filtration (Filtration A/II).

In a test experiment by thin-layer chromatography, no traces of 2-keto-gulonate could be shown in the filtrate (Filtrate A), but could in the filter residue (Filter residue A). The latter had a dry weight of 10.7 g. The ascorbate obtained (Product A) had a dry weight of 88.35 grams, which corresponds to 89.82% of the theoretically possible yield. The purity of the ascorbate obtained could be determined by iodine titration at 96.9% and by GC determination at 99.87%.

The filter residue (10.7 g) (Filter residue A) is treated in a parallel solution, with 24 cc methanol, with addition of 1.3 cc $H_2SO_4$, at 67° to 68° C. for 30 minutes (Esterification B). Then it is dosed with 1.3 g sodium bicarbonate and stirred one hour at 50° C. (Precipitation B). The ppt. formed (6.7 g) is filtered out (Filtration B/I), the filtrate residue (Filter residue B) is discarded. The filtrate (Filtrate B) is then lactonized (Lactonization B) for three hours with bicarbonate (Lactonization B) and finally isolated by filtration (Filtration B/II).

In the test experiment in this way, 4.4 grams dry ascorbate (Product B) were obtained. This corresponds to a yield, based on the 100 grams of raw material put in, of 4.62%. The purity could be determined by iodine titration at 96.4% and by GC determination at 99%.

The total yield in the test experiment was 94.44% (Products A+B), the average purity of the total product 99.8% (GC determination).

EXAMPLE 2

The same esterification mixture as in Example 1 is kept for an hour at 67° to 68° C. (Esterification A) and then stirred with 12.5 g sodium bicarbonate for two hours at 60° C. (Precipitation A).

In a test experiment, filtration (Filtration A/I) gave 9.4 grams filter residue (Filter residue A). In the filtrate (Filtrate A), no 2-keto gulonate could be shown. From the filtrate (Filtrate A) could be prepared, as in Example 1, 88.35 g (90.83% of theory) dry sodium ascorbate (Product A), with a purity of 94.4% (iodine titration) or 99.6% (GC determination).

The filter residue (Filter residue A) is esterified again, as in Example 1, in 24 cc methanol with 1.3 cc $H_2SO_4$, for one hour (Esterification B), and the solution is treated with 1.3 g sodium bicarbonate at 60° C. for one-half hour (Precipitation B). The ppt. is filtered out and the filter residue discarded.

In the test, after precipitation and filtration, 6.3 grams filter residue were obtained. In the filtrate (Filtrate B), 2-keto gulonate could no longer be detected. From the filtrate (Filtrate B) could be prepared, as in Example 1, 3.6 g dry sodium ascorbate (Product B), corresponding to a yield of 3.57% of theory, with a purity of 91% (iodine titration) or 98.7% (GC determination).

The total yield in the experiment was 94.4% (Products A and B), and the average purity of the total product 99.6% (GC determination).

EXAMPLE 3

To a mixture of 100 g 2-keto-L-gulonic acid monohydrate, 325 cc methanol and 5.5 cc $H_2SO_4$ are added 10 g filter residue, such as filter residue (Filter residue A) in Example 1. The solution is esterified for one hour at 67° to 68° C. (Esterification A), and then treated, as in the previous examples, with 13.5 g sodium bicarbonate.

In one test, after precipitation and filtration, 15.8 g filter residue were obtained. From the filtrate could be prepared by lactonization, as in the previous example, 91.64 grams dry sodium ascorbate, corresponding to a yield of 93.52% of theory, with a purity of 93.7% (iodine titration) or 99.9% (GC determination).

EXAMPLE 4

One hundred grams 2-keto gulonic acid monohydrate is treated as in Example 1, (esterification A, precipitation A, filtration A/I). The filter residue (Filter residue A) is then treated as in Example 1 (esterification B, precipitation B, filtration B/I). A second filtrate (Filtrate B) is given and there is another filter residue (Filter residue B). The latter is discarded. In variation from Example 1, the two filtrates (Filtrates A and B) are mixed and boiled with bicarbonate for two hours.

In one test, 90.1 grams dry ascorbate, corresponding to a yield of 94.22%, could be obtained, with a purity of 96.0 (iodine titration) or 99.7% (GC determination).

EXAMPLE 5

A mixture (50 g) of 2-keto-L-gulonic acid (51.57%) and sodium-2-keto-gulonate (48.43%) is suspended in methanol (130 ml), and 4.5 ml concentrated sulfuric acid added. The suspension is heated one hour in a reflux with stirring, and then filtered to remove the resultant sodium sulfate (4.77 g). Sodium bicarbonate (7.0 g) is added to the filtrate and the suspension is heated one more hour with stirring in a reflux.

Then it is filtered again. 8.7 g sediment are obtained. For the lactonization, more sodium bicarbonate (15 g) is added to the filtrate. The suspension is heated, with stirring, for two hours in a reflux. The resultant sodium ascorbate is separated by filtration. 38.35 g dry end product, with a purity of 94.5% are obtained.

EXAMPLE 6

2-keto-L-gulonic acid monohydrate (300 g, 1.415 mol) is put into a 1,000 ml glass reaction vessel, and methanol (780 ml) added. Sulfuric acid (3 ml) is added in drops with stirring, and the reaction solution is heated (68° C.) for an hour with stirring in a reflux. Then the solution is cooled to 60° C. 31.2 grams sodium bicarbonate are added, and stirring with heating in a reflux is continued for another hour. The precipitate obtained is separated by filtration. It contains 33.19 g dry sediment, which contains 48% of the 2-keto-L-gulonic acid as sodium salt. The filtrate is cooled to 5° C. and the pure 2-keto-L-gulonic acid methyl ester precipitated is filtered out again and dried (190 g). 20 g of this pure ester are dissolved in methanol (80 ml), and sodium bicarbonate (7.2 g) added. The suspension is heated in a reflux with stirring for two hours. The resultant ascorbate is filtered out, washed with 10 ml methanol and then dried. 19.27 g dry product are obtained with a purity of 98.15%.

To further increase its purity, the ascorbate obtained is recrystallized. For this, it is dissolved in 20 ml distilled water. The solution is filtered and then treated with 40 ml methanol. The resultant suspension is cooled to 0° C., and the desired product filtered out and dried. 14.44 grams pharmaceutically pure sodium ascorbate is obtained with a purity of 99.34%.

We claim:

1. A process for the production of sodium or potassium L-ascorbate comprising the steps of:
    preparing an esterification solution comprising 2-keto-L-gulonic acid monohydrate dissolved in methanol in the presence of at least a catalytic amount of sulfuric acid;
    allowing the esterification reaction of the 2-keto-L-gulonic acid monohydrate to proceed under conditions and for a time effective to obtain a reaction mixture comprising 2-keto-L-gulonic acid methyl ester and unesterified 2-keto-L-gulonic acid monohydrate;
    stopping said esterification reaction prior to establishing esterification equilibrium;
    adding to said reaction mixture a first amount of sodium or potassium bicarbonate effective to neutralize the unesterified 2-keto-L-gulonic acid monohydrate causing precipitation of the acid monohydrate, said first amount being insufficient to cause substantial lactonization of the 2-keto-L-gulonic acid methyl ester
    separating said precipitate from said reaction mixture;
    adding to said reaction mixture an additional amount of sodium or potassium bicarbonate in an amount effective to lactonize the 2-keto-L-gulonic acid methyl ester in said reaction mixture and to form a product suspension comprising sodium L-ascorbate or potassium L-ascorbate; and
    separating sodium L-ascorbate or potassium L-ascorbate from said product suspension.

2. A process according to claim 1 with the distinction that said esterification solution comprising 2-keto-L-gulonic acid monohydrate also comprises sodium-2-keto-L-gulonate, and that the total amount of concentrated sulfuric acid is such that it suffices, substantially, also for the conversion of the sodium 2-keto-L-gulonate into 2-keto-L-gulonic acid.

3. A process according to claim 2, with the distinction that the sodium sulfate occurring in the conversion of the sodium-2-keto-L-gulonate into 2-keto-L-gulonic acid is filtered from said reaction mixture before the bicarbonate is added to said reaction mixture.

4. A process according to claim 3, with the distinction that the esterification solution is prepared with the addition of concentrated sulfuric acid in two steps, (a) only about as much concentrated sulfuric acid is added as is necessary for the conversion of sodium-2-keto-L-gulonate into 2-keto-L-gulonic acid and (b) the amount of concentrated sulfuric acid catalyzing the esterification is only added after filtering the resultant sodium sulfate from the esterification solution.

5. A process according to claim 1, with the distinction that the esterification of the 2-keto-gulonic acid with methanol is carried out in only 15 to 90 minutes, according to the degree of impurity of the raw product, at 60° to 75° C. to a degree of esterification of 87–91%.

6. A process according to claim 1, with the distinction that after the addition of said first amount of sodium or potassium bicarbonate to the reaction mixture, the mixture is stirred at a constant temperature of about 60° C. for a time range of about 30 to 120 minutes, the precipitation of neutralized 2-keto-L-gulonic acid taking place in said time range.

7. A process according to claim 1, with the distinction that the reaction mixture remaining after separating the precipitate is cooled to a temperature in the range between 0° and 5° C., and 2-keto-L-gulonic acid methyl ester precipitated in this way is separated from the reaction mixture.

8. A process according to claim 7, with the distinction that the sodium or potassium bicarbonate necessary for lactonizing the 2-keto-L-gulonic acid methyl ester is added to the reaction mixture remaining after the separation of the precipitate of said monohydrate and the separation of the 2-keto-L-gulonic acid methyl ester precipitated by lowering the temperature.

9. A process according to claim 7, with the distinction that the 2-keto-L-gulonic acid methyl ester is dissolved again in methanol, and that the sodium or potassium bicarbonate necessary for lactonizing the 2-keto-L-gulonic acid methyl ester is added to this solution.

10. A process according to claim 1, with the distinction that the reaction mixture of 2-keto-L-gulonic acid methyl ester, to which more sodium or potassium bicarbonate has been added in order to lactonize this ester, is cooked, after this addition, for 30 to 180 minutes at 60° to 67° C.

11. A process according to claim 1, with the distinction that the precipitate of neutralized 2-keto-L-gulonic acid is introduced into the process again, as raw material, instead of fresh 2-keto-L-gulonic acid monohydrate.

12. A process according to claim 10, with the distinction that the precipitate of neutralized 2-keto-L-gulonic acid is used in the preparation of a separate esterification solution comprising said neutralized 2-keto-L-gulonic acid monohydrate dissolved in methanol in the presence of at least a catalytic amount of sulfuric acid, and that the precipitate from the neutralization of this solution is discarded.

* * * * *